United States Patent [19]
Guracar

[11] Patent Number: 6,001,063
[45] Date of Patent: Dec. 14, 1999

[54] ULTRASONIC IMAGING METHOD AND APPARATUS FOR PROVIDING DOPPLER ENERGY CORRECTION

[75] Inventor: Ismayil Guracar, Redwood City, Calif.

[73] Assignee: Acuson Corporation, Mountain View, Calif.

[21] Appl. No.: 09/103,328

[22] Filed: Jun. 23, 1998

[51] Int. Cl.⁶ .................................................. A61B 08/00
[52] U.S. Cl. ............................................................ 600/453
[58] Field of Search ..................................... 600/453, 455, 600/454, 456, 457, 448, 440; 128/916; 73/462

[56] References Cited

U.S. PATENT DOCUMENTS

| | | |
|---|---|---|
| 4,850,364 | 7/1989 | Leavitt . |
| 5,349,525 | 9/1994 | Dunki-Jacobs et al. . |
| 5,386,830 | 2/1995 | Powers et al. ............................ 600/455 |
| 5,544,658 | 8/1996 | Kim et al. ................................ 600/455 |
| 5,549,111 | 8/1996 | Wright et al. .............................. 73/642 |
| 5,609,155 | 3/1997 | Guracar . |
| 5,709,210 | 1/1998 | Green et al. ............................. 600/453 |
| 5,860,928 | 1/1999 | Wong et al. ............................. 600/455 |

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasonic imaging system generates a corrected Doppler energy signal as a function of both Doppler energy and Doppler velocity to correct for loss of sensitivity associated with the gradual roll off response characteristic of many clutter filters. Additionally, the corrected Doppler energy signal is generated as a function of Doppler variance to prevent enhancement of noisy samples.

33 Claims, 2 Drawing Sheets

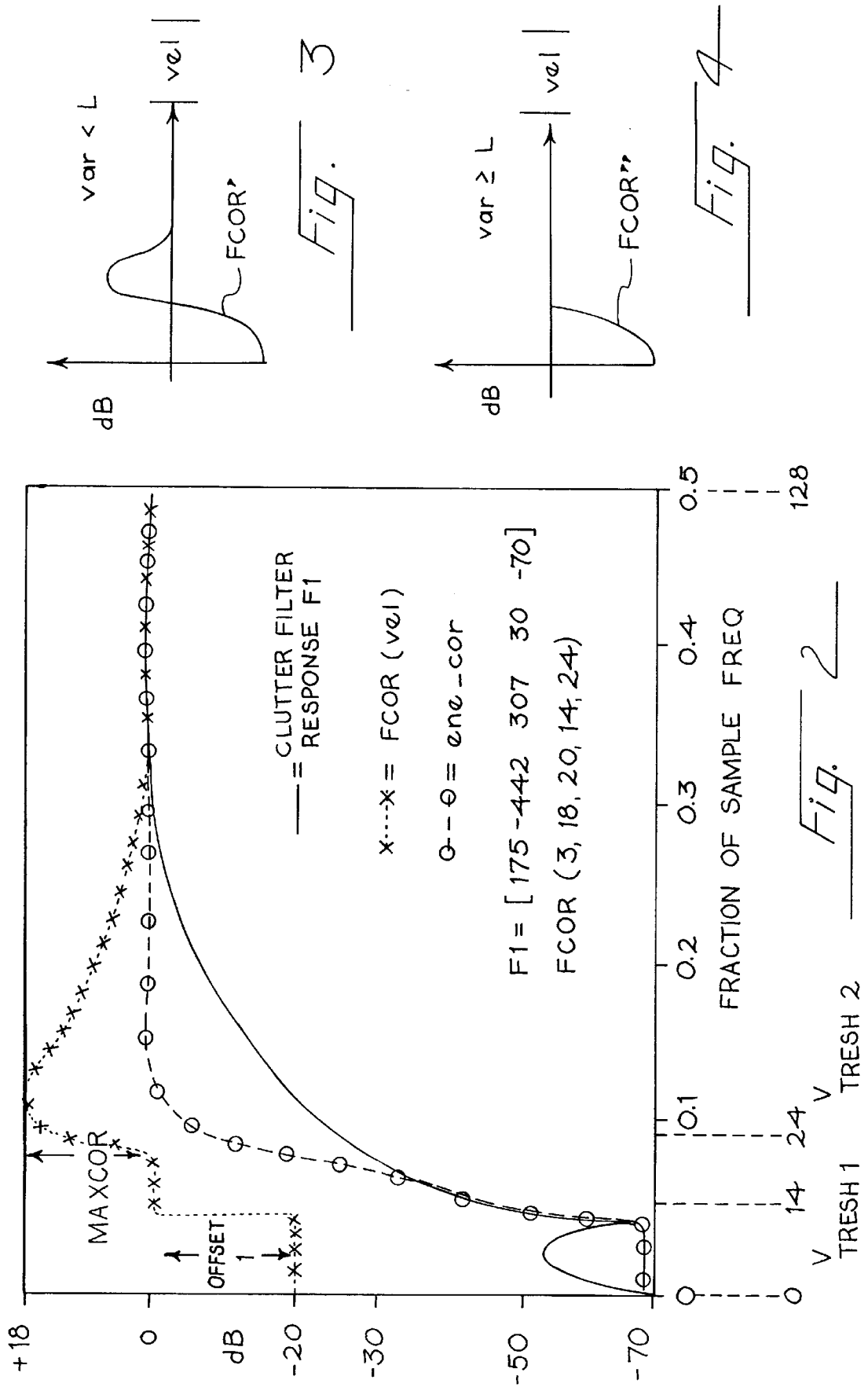

ULTRASONIC IMAGING METHOD AND APPARATUS FOR PROVIDING DOPPLER ENERGY CORRECTION

BACKGROUND

This invention relates to the field of ultrasonic imaging, and in particular to medical diagnostic Doppler ultrasonic imaging.

It is conventional in the field of medical ultrasonic imaging to provide images of various Doppler parameters including Doppler velocity and Doppler energy. See for example, Leavitt U.S. Pat. No. 4,850,364, Dunki-Jacobs U.S. Pat. No. 5,349,525, and Guracar U.S. Pat. No. 5,609,155. Typically, the beamformed receive signal is passed through a clutter filter that rejects echo signals associated with slowly moving or non-moving scattering sites. The clutter-filtered receive signal is then applied to a Doppler processor that typically uses an autocorrelation estimator to estimate Doppler parameters such as Doppler energy, Doppler velocity and Doppler variance.

One problem of the prior art is that the gradual roll off of the clutter filter can have an adverse effect on the accuracy of various Doppler parameters, particularly Doppler energy.

SUMMARY

The present invention is directed to improved methods and systems for improving sensitivity of Doppler parameters such as Doppler energy to low velocity scatterers.

The present invention is defined by the following claims, and nothing in this section should be taken as a limitation on those claims. By way of introduction, the preferred embodiment described below applies a correction to a Doppler energy signal, and this correction varies as a function of the measured Doppler velocity. By properly adjusting the correction as a function of velocity, a more accurate estimate of Doppler energy can be provided with increased sensitivity to low velocity scatterers. The embodiment described below also acts to reduce sensitivity to Doppler energy measurements in the stop band of the clutter filter and to reduce the contribution of scatterers that are characterized by a high Doppler variance.

BRIEF DESCRIPTION OF THE DRAWINGS

FIG. 2 is a graph showing a clutter filter response, F1, a correction function, fcor, and a corrected Doppler energy, ene_cor, all as functions of Doppler velocity.

FIGS. 3 and 4 are graphs of two alternate correction functions, fcor' and fcor", that can be used in the embodiment of FIG. 1.

DETAILED DESCRIPTION OF THE PRESENTLY PREFERRED EMBODIMENTS

Figure 1:
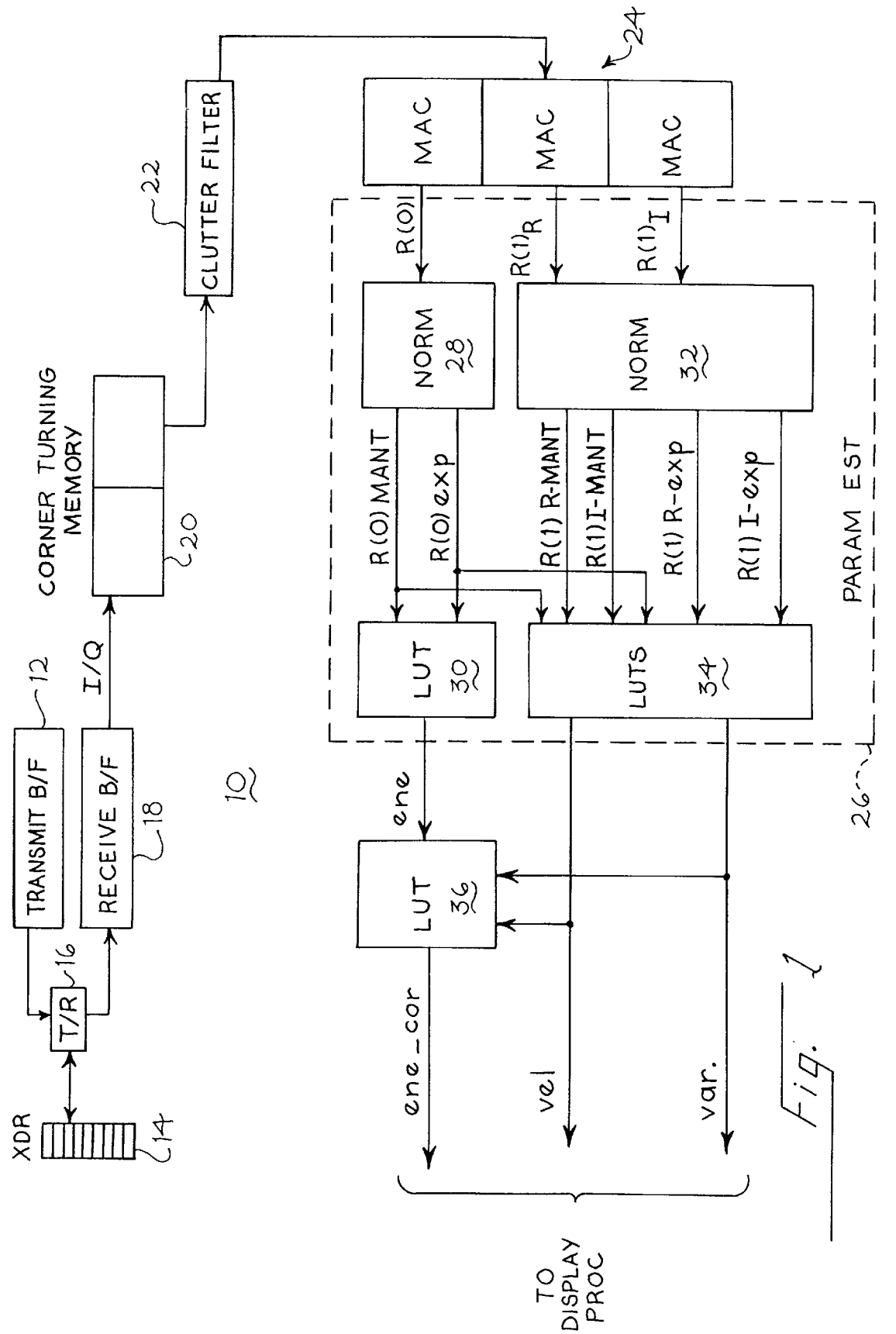
FIG. 1 is a block diagram of an ultrasonic imaging system that incorporates a presently preferred embodiment of this invention.

Turning now to the drawings, FIG. 1 shows a block diagram of an ultrasonic imaging system 10 that incorporates a preferred embodiment of this invention.

The system 10 includes a transmit beamformer 12 that is coupled to a transducer array 14 by a transmit/receive switch 16. The switch 16 also connects the transducer array 14 with a receive beamformer 18. Beamformed receive signals from the receive beamformer 18 in I/Q format are applied to a corner turning memory 20, which applies receive signals at a common range from multiple separate scan lines to a clutter filter 22.

The clutter filter 22 can for example be an FIR filter designed to suppress receive signals associated with slowly moving scatterers. Generally, the clutter filter 22 can have a response curve that varies as a function of the Doppler velocity such that receive signals associated with a Doppler velocity below a threshold are suppressed and receive signals associated with Doppler velocities well above the threshold are not. It is advantageous to provide the clutter filter 22 with a sharp cutoff characteristic, but such filters are generally associated with a large number of taps and consequently a longer flow sample count. For this reason, engineering compromises often result in clutter filters having a relatively gradual roll off as shown by the response curve F1 of in FIG. 2.

The filtered output of the clutter filter 22 is applied to a set of three multiply accumulators 24. The multiply accumulators 24 generate output signals for the zeroth lag R(0) and the first lag R(1). As is conventional, the zeroth lag R(0) is a real number calculated in accordance with Equation 1, where x(k) is the complex I/Q receive signal at time k supplied by the clutter filter 22:

$$R(0) = \sum_{k=1}^{N} |x(k)|^2. \tag{Eq. 1}$$

The first lag signal R(1) is calculated according to Equation 2, where the asterisk is used to denote a complex conjugate:

$$R(1) = \sum_{k=2}^{N} x(k)x^*(k-1). \tag{Eq. 2}$$

The first lag signal R(1) is a complex number that takes the following form:

$$R(1) = R(1)_R + \sqrt{-1}\, R(1)_I. \tag{Eq. 3}$$

FIG. 1 identifies the real and imaginary portions of the first lag signal R(1) as $R(1)_R$ and $R(1)_I$, respectively.

The signal R(0) is applied to a normalizer 28 that generates as output signals a normalized R(0) in the form $R(0)_{mant}$ and $R(0)_{exp}$. In this case, $R(0)_{mant}$ corresponds to the mantissa and $R(0)_{exp}$ corresponds to the exponent of 2 that characterizes the normalized zeroth lag signal. For example, if the normalized value of R(0) were 310 (equal to $1.21 \times 2^8$), $R(0)_{mant}$ would equal 1.21 and $R(0)_{exp}$ would equal 8.

The normalized signals supplied by the normalizer 28 are applied to a lookup table 30 that generates as an output signal a measure of Doppler energy, ene, according to the following equation:

$$\text{ene} = 10 \cdot \log_{10}(R(0)). \tag{Eq. 4}$$

Similarly, the first lag signals $R(1)_R$ and $R(1)_I$ are applied to a normalizer 32 that applies normalized mantissa and exponent signals for both components of R(1) to lookup table 34. The lookup table 34 generates as output signals a Doppler velocity signal, vel, and a Doppler variance signal, var, according to the following equations:

$$vel = \arctan\left(\frac{R(1)_I}{R(1)_R}\right), \quad \text{(Eq. 5)}$$

$$var = 1 - \frac{|R(1)|}{R(0)}. \quad \text{(Eq. 6)}$$

The features of the system 10 described above can be implemented in any suitable form, using conventional technology well known to those skilled in the art. For example, the beamformers 12, 18 can be digital or analog beamformers as desired. The transducer array 14 can take any suitable form, including 1, 1.5 or 2 dimensional arrays, of the phased array or the moving transducer type. The elements 28–34 make up a parameter estimator 26 that can be implemented in any desired technology. See for example the parameter estimator 40 of Guracar U.S. Pat. No. 5,609,155, which is hereby incorporated by reference.

Because the clutter filter 22 has a response with a gradual rolloff characteristic, the values of Doppler energy, ene, are inaccurately low near the cutoff frequency of the clutter filter. The system of FIG. 1 corrects this error with the lookup table 36. The lookup table 36 receives as addressing inputs, the Doppler energy signal, ene, the Doppler velocity signal, vel, and the Doppler variance signal, var, and generates as an output signal a corrected energy signal, ene_cor, according to the following formula:

$$ene\_cor = ene + fcor(vel, var). \quad \text{(Eq. 7)}$$

The function, fcor, that is added to ene in the lookup table 36 can take the form shown in FIG. 2. In this example, fcor can be considered a function of five variables: fcor (index, maxcor, thresh1, $v_{thresh1}$, $v_{thresh2}$). The first variable, index, indicates that fcor is adapted for use with clutter filter response F1, as shown in FIG. 2. This clutter filter response is characteristic of an FIR response with tap weights [175-442 307 30-70].

The second parameter, maxcor, indicates the maximum positive correction supplied by the correction function, fcor, in this case 18 dB. Note that the maximum correction is applied at relatively low Doppler velocities near the lower edge of the clutter filter passband. In the clutter filter response F1 of FIG. 2, the stop band extends from 0 to about 0.05, and the passband extends from about 0.05 to 0.5. In this case the units of the X axis are the absolute value of Doppler frequency divided by the sample frequency. Thus, the positive correction provided by fcor near the lower edge of the passband increases ene_cor in the region of the gradual rolloff of the clutter filter response, F1.

The third parameter, offset1, indicates the amount of negative correction provided by fcor for samples in the stop band of the clutter filter response. In this case, offset1 equals −20 dB. This ensures that leakage through the stop band of the clutter filter is further suppressed.

The fourth parameter, $v_{thresh1}$, defines the upper limit at which offset1 will be applied to suppress the values of ene_cor. In this example, a Doppler velocity of 0.5 as a fraction of sample frequency corresponds to 128, and 14 therefore corresponds approximately to 0.05.

The fifth parameter, $v_{thresh2}$, indicates the lowest Doppler velocity for which a positive correction is applied to ene_cor.

Note from FIG. 2 that the curve for ene_cor is much closer to the desired, sharp cutoff characteristic than is the clutter filter response F1. In effect, the curve for ene_cor shows the effective frequency response after correction. Corrections for very low Doppler energy signals are limited since the velocity estimate for these signals is often unreliable. The correction function fcor of FIG. 2 operates to increase ene_cor over a portion of the passband of the clutter filter and also to decrease ene_cor over at least part of the stop band of the clutter filter. In this context, increasing and decreasing are measured with respect to the uncorrected Doppler energy signal, ene.

The corrected Doppler energy signal, ene_cor, and the velocity and variance signals, vel, var, can then be sent to an energy weighted persistence block as described in U.S. Pat. No. 5,609,155 for further processing, including conventional thresholding, spatial smoothing, scan conversion, color mapping and display as is known in the art.

Though not required, it is preferable that the lookup table 36 provide a correction function that also varies with Doppler variance. If Doppler variance is low, indicating a relatively high precision measurement of Doppler energy, the correction function fcor of FIG. 2 or fcor' of FIG. 3 can be used. On the other hand, if variance is relatively high, i.e. greater than or equal to a threshold level L, a modified correction function fcor" can be applied by the lookup table 36, as shown in FIG. 4. The modified correction function fcor" continues to suppress Doppler energy in the region of the stop band of the clutter filter, but it no longer increases Doppler energy in regions of the passband of the clutter filter. In this way, relatively noisy Doppler energy samples are not increased, and noise problems are reduced.

It should be clear that the modified correction function fcor" of FIG. 4 reduces any increase to ene_cor associated with high variance samples.

Of course, it should be recognized that many changes and modifications can be made to the preferred embodiment described above. For example, it is not required in all embodiments that the Doppler energy be first calculated, and then corrected to form the corrected energy signal. The lookup tables 30 and 36 can be replaced with a single lookup table that generates the output ene_cor. In general, a corrected Doppler energy signal is generated from a first signal that varies as a function of Doppler energy and a second signal that varies as a function of Doppler velocity. The first signal can take many forms, and may correspond to the Doppler energy signal, ene, as in FIG. 1, or to the zeroth lag signal R(0) in an embodiment where the lookup tables 30 and 36 are replaced with a single lookup table. Similarly, the second signal that varies as a function of Doppler velocity may correspond to the Doppler velocity signal, vel, or to other signals that vary as a function of the first lag signal R(1).

Furthermore, it is not essential in all embodiments that lookup tables be used to implement the desired correction. Lookup tables provide the advantage that they can readily be programmed as appropriate for particular applications. However, if desired, other function generators can be used, including those implemented with analog circuitry or with digital calculators. Any of these implementations can be considered examples of generating means that generate a corrected Doppler energy signal as a function of a first signal that varies as a function of Doppler energy and a second signal that varies as a function of Doppler velocity.

As used herein, the terms "Doppler energy" and "Doppler velocity" are intended broadly to encompass any signals that vary as a function of the respective Doppler parameters. For example, a Doppler energy signal can vary as a linear, logarithmic, exponential, or other function of Doppler energy. Similarly, a Doppler velocity signal can vary as a linear, logarithmic, exponential, or other function of Doppler velocity.

The term "Doppler variance" is intended broadly to encompass any signal that provides a measure of estimation quality or estimation confidence of a Doppler signal, such as, for example, signal to noise ratio.

The term "signal" is intended broadly to encompass one or more signals. For example a complex signal can include two components, real and imaginary, as described above.

The term "function of" is intended broadly such that a first variable is a function of a second variable, whether or not other parameters are also involved. Thus, a correction function fcor (vel, var) is said to be a function of vel.

The term "responsive to" is intended broadly to encompass systems that are responsive either directly or indirectly to one another. For example, a first system is said to be responsive to a second system even in the event of intermediate processing between the first and second systems.

A signal such as a Doppler energy signal is said to be decreased when it is changed to correspond to a lower Doppler energy, regardless of the representation used. Thus, a Doppler energy signal may be decreased even if the absolute amplitude of the signal is increased, for example in a representation where higher amplitude signals correspond to lower Doppler energies.

The foregoing detailed description has described only a few of the many forms that this invention can take. For this reason, it is intended that this description be regarded as an illustration of selected forms of the invention, and not as a definition of the invention. It is only the following claims, including all equivalents, that are intended to define the scope of this invention.

I claim:

1. A method for adjusting a Doppler ultrasound signal comprising the following steps:
    (a) obtaining a plurality of Doppler ultrasound signals comprising a Doppler energy signal and an associated Doppler velocity signal; and
    (b) generating a corrected Doppler energy signal which differs from the Doppler energy signal in a direction determined as a function of the Doppler velocity signal.

2. A method of generating a corrected Doppler ultrasound signal comprising the following steps:
    (a) obtaining a first signal that varies as a function of Doppler energy and a second signal that varies as a function of Doppler velocity; and
    (b) generating a corrected Doppler energy signal which differs from the first signal in a direction determined as a function of the second signal.

3. The method of claim 1 or 2 wherein step (a) comprises the steps of filtering a plurality of ultrasound receive signals with a clutter filter and applying the clutter-filtered receive signals to an autocorrelation estimator.

4. The method of claim 3 wherein the clutter filter is characterized by a pass band, and wherein step (b) comprises the step of increasing the corrected Doppler energy signal over a portion of the pass band.

5. The method of claim 3 wherein the clutter filter is characterized by a stop band, and wherein step (b) comprises the step of decreasing the corrected Doppler energy signal over at least a portion of the stop band.

6. The method of claim 3 wherein the clutter filter is characterized by a stop band and a pass band, and wherein step (b) comprises the steps of (1) decreasing the corrected Doppler energy signal over at least a portion of the stop band, and (2) increasing the corrected Doppler energy signal over a portion of the pass band.

7. An ultrasound imaging system comprising:
    a Doppler parameter estimator operative to generate a first signal that varies as a function of Doppler energy and a second signal that varies as a function of Doppler velocity; and
    means for generating a corrected Doppler energy signal which differs from the first signal in a direction determined as a function of the second signal.

8. The invention of claim 7 wherein the ultrasound imaging system further comprises a clutter filter, and wherein the Doppler parameter estimator comprises an autocorrelation estimator responsive to the clutter filter.

9. The invention of claim 8 wherein the clutter filter is characterized by a pass band, and wherein the generating means operates to increase the corrected Doppler energy signal over a portion of the pass band as a function of the second signal.

10. The invention of claim 8 wherein the clutter filter is characterized by a stop band, and wherein the generating means operates to decrease the corrected Doppler energy signal over at least a portion of the stop band as a function of the second signal.

11. The invention of claim 8 wherein the clutter filter is characterized by a stop band and a pass band, and wherein the generating means operates (1) to decrease the corrected Doppler energy signal over at least a portion of the stop band as a function of the second signal, and (2) to increase the corrected Doppler energy signal over a portion of the pass band as a function of the second signal.

12. The invention of claim 9 wherein the Doppler parameter estimator is additionally operative to generate a third signal that varies as a function of Doppler variance, and wherein the generating means comprises means for modifying increases to the corrected Doppler energy signal as a function of the third signal to reduce increases to the corrected Doppler energy signal associated with high Doppler variance.

13. An ultrasound imaging system comprising:
    a Doppler parameter estimator operative to generate a first signal that varies as a function of Doppler energy and a second signal that varies as a function of Doppler velocity; and
    means for generating a corrected Doppler energy signal as a function of both the first signal and the second signal;
    wherein the Doppler parameter estimator is operative to generate a third signal that varies as a function of Doppler variance, and wherein the generating means generates the corrected Doppler energy signal as a function of the first, second and third signals.

14. An ultrasound imaging system comprising:
    a Doppler parameter estimator operative to generate a first signal that varies as a function of Doppler energy and a second signal that varies as a function of Doppler velocity; and
    a look up table responsive to both the first signal and the second signal and operative to generate a corrected Doppler energy signal.

15. The invention of claim 14 wherein the ultrasound imaging system further comprises a clutter filter, and wherein the Doppler parameter estimator comprises an autocorrelation estimator responsive to the clutter filter.

16. The invention of claim 15 wherein the clutter filter is characterized by a pass band, and wherein the look up table operates to increase the corrected Doppler energy signal over a portion of the pass band as a function of the second signal.

17. The invention of claim 15 wherein the clutter filter is characterized by a stop band, and wherein the look up table operates to decrease the corrected Doppler energy signal over at least a portion of the stop band as a function of the second signal.

18. The invention of claim 15 wherein the clutter filter is characterized by a stop band and a pass band, and wherein the look up table operates (1) to decrease the corrected Doppler energy signal over at least a portion of the stop band as a function of the second signal, and (2) to increase the corrected Doppler energy signal over a portion of the pass band as a function of the second signal.

19. The invention of claim 14 wherein the Doppler parameter estimator is operative to generate a third signal that varies as a function of Doppler variance, and wherein the look up table generates the corrected Doppler energy signal as a function of the first, second and third signals.

20. The invention of claim 16 wherein the Doppler parameter estimator is additionally operative to generate a third signal that varies as a function of Doppler variance, and wherein the look up table comprises means for modifying increases to the corrected Doppler energy signal as a function of the third signal to reduce increases to the corrected Doppler energy signal associated with high Doppler variance.

21. The invention of claim 14 wherein the corrected Doppler signal differs from the first signal in a direction determined as a function of the second signal.

22. A method for adjusting a Doppler ultrasound signal comprising the following steps:
(a) obtaining a plurality of Doppler ultrasound signals comprising a Doppler energy signal and an associated Doppler velocity signal; and
(b) generating a corrected Doppler energy signal as a function of the Doppler energy signal and the Doppler velocity signal;
wherein step (a) comprises the steps of filtering a plurality of ultrasound receive signals with a clutter filter and applying the clutter-filtered receive signals to an auto-correlation estimator;
wherein the clutter filter is characterized by a pass band, and wherein step (b) comprises the step of increasing the corrected Doppler energy signal over a portion of the pass band.

23. A method of generating a corrected Doppler ultrasound signal comprising the following steps:
(a) obtaining a first signal that varies as a function of Doppler energy and a second signal that varies as a function of Doppler velocity; and
(b) generating a corrected Doppler energy signal as a function of both the first signal and the second signal;
wherein step (a) comprises the steps of filtering a plurality of ultrasound receive signals with a clutter filter and applying the clutter-filtered receive signals to an auto-correlation estimator;
wherein the clutter filter is characterized by a pass band, and wherein step (b) comprises the step of increasing the corrected Doppler energy signal over a portion of the pass band.

24. A method for adjusting a Doppler ultrasound signal comprising the following steps:
(a) obtaining a plurality of Doppler ultrasound signals comprising a Doppler energy signal and an associated Doppler velocity signal; and
(b) generating a corrected Doppler energy signal as a function of the Doppler energy signal and the Doppler velocity signal;
wherein step (a) comprises the steps of filtering a plurality of ultrasound receive signals with a clutter filter and applying the clutter-filtered receive signals to an auto-correlation estimator;
wherein the clutter filter is characterized by a stop band, and wherein step (b) comprises the step of decreasing the corrected Doppler energy signal over at least a portion of the stop band.

25. A method of generating a corrected Doppler ultrasound signal comprising the following steps:
(a) obtaining a first signal that varies as a function of Doppler energy and a second signal that varies as a function of Doppler velocity; and
(b) generating a corrected Doppler energy signal as a function of both the first signal and the second signal;
wherein step (a) comprises the steps of filtering a plurality of ultrasound receive signals with a clutter filter and applying the clutter-filtered receive signals to an auto-correlation estimator;
wherein the clutter filter is characterized by a stop band, and wherein step (b) comprises the step of decreasing the corrected Doppler energy signal over at least a portion of the stop band.

26. A method for adjusting a Doppler ultrasound signal comprising the following steps:
(a) obtaining a plurality of Doppler ultrasound signals comprising a Doppler energy signal and an associated Doppler velocity signal; and
(b) generating a corrected Doppler energy signal as a function of the Doppler energy signal and the Doppler velocity signal;
wherein step (a) comprises the steps of filtering a plurality of ultrasound receive signals with a clutter filter and applying the clutter-filtered receive signals to an auto-correlation estimator;
wherein the clutter filter is characterized by a stop band and a pass band, and wherein step (b) comprises the steps of (1) decreasing the corrected Doppler energy signal over at least a portion of the stop band, and (2) increasing the corrected Doppler energy signal over a portion of the pass band.

27. A method of generating a corrected Doppler ultrasound signal comprising the following steps:
(a) obtaining a first signal that varies as a function of Doppler energy and a second signal that varies as a function of Doppler velocity; and
(b) generating a corrected Doppler energy signal as a function of both the first signal and the second signal;
wherein step (a) comprises the steps of filtering a plurality of ultrasound receive signals with a clutter filter and applying the clutter-filtered receive signals to an auto-correlation estimator;
wherein the clutter filter is characterized by a stop band and a pass band, and wherein step (b) comprises the steps of (1) decreasing the corrected Doppler energy signal over at least a portion of the stop band, and (2) increasing the corrected Doppler energy signal over a portion of the pass band.

28. A method for adjusting a Doppler ultrasound signal comprising the following steps:
(a) obtaining a plurality of Doppler ultrasound signals comprising a Doppler energy signal and an associated Doppler velocity signal; and
(b) generating a corrected Doppler energy signal as a function of the Doppler energy signal and the Doppler velocity signal;
wherein step (b) comprises the step of generating the corrected Doppler energy signal as a function of a Doppler variance signal.

29. The method of claim 28 wherein step (b) comprises the step of modifying the increasing step as a function of a Doppler variance signal to reduce increases to the corrected Doppler energy signal associated with high Doppler variance signals.

30. A method of generating a corrected Doppler ultrasound signal comprising the following steps:
   (a) obtaining a first signal that varies as a function of Doppler energy and a second signal that varies as a function of Doppler velocity; and
   (b) generating a corrected Doppler energy signal as a function of both the first signal and the second signal;
   wherein step (b) comprises the step of generating the corrected Doppler energy signal as a function of a Doppler variance signal.

31. An ultrasound imaging system comprising:
   a Doppler parameter estimator operative to generate a first signal that varies as a function of Doppler energy and a second signal that varies as a function of Doppler velocity; and
   means for generating a corrected Doppler energy signal as a function of both the first signal and the second signal;
   wherein the ultrasound imaging system further comprises a clutter filter, and wherein the Doppler parameter estimator comprises an autocorrelation estimator responsive to the clutter filter;
   wherein the clutter filter is characterized by a pass band, and wherein the generating means operates to increase the corrected Doppler energy signal over a portion of the pass band as a function of the second signal.

32. An ultrasound imaging system comprising:
   a Doppler parameter estimator operative to generate a first signal that varies as a function of Doppler energy and a second signal that varies as a function of Doppler velocity; and
   means for generating a corrected Doppler energy signal as a function of both the first signal and the second signal;
   wherein the ultrasound imaging system further comprises a clutter filter, and wherein the Doppler parameter estimator comprises an autocorrelation estimator responsive to the clutter filter;
   wherein the clutter filter is characterized by a stop band, and wherein the generating means operates to decrease the corrected Doppler energy signal over at least a portion of the stop band as a function of the second signal.

33. An ultrasound imaging system comprising:
   a Doppler parameter estimator operative to generate a first signal that varies as a function of Doppler energy and a second signal that varies as a function of Doppler velocity; and
   means for generating a corrected Doppler energy signal as a function of both the first signal and the second signal;
   wherein the ultrasound imaging system further comprises a clutter filter, and wherein the Doppler parameter estimator comprises an autocorrelation estimator responsive to the clutter filter;
   wherein the clutter filter is characterized by a stop band and a pass band, and wherein the generating means operates (1) to decrease the corrected Doppler energy signal over at least a portion of the stop band as a function of the second signal, and (2) to increase the corrected Doppler energy signal over a portion of the pass band as a function of the second signal.

* * * * *